United States Patent
Hoar et al.

Patent Number: 6,032,063
Date of Patent: Feb. 29, 2000

[54] DISTRIBUTED RESISTANCE LEADWIRE HARNESS ASSEMBLY FOR PHYSIOLOGICAL MONITORING DURING MAGNETIC RESONANCE IMAGING

[75] Inventors: Edward F. Hoar, Centerville; Mark L. Meister, Hamilton, both of Ohio

[73] Assignee: Vital Connections, Inc., Tipp City, Ohio

[21] Appl. No.: 09/203,239

[22] Filed: Dec. 1, 1998

Related U.S. Application Data

[60] Provisional application No. 60/069,147, Dec. 9, 1997.

[51] Int. Cl.[7] .................................................. A61B 5/04
[52] U.S. Cl. ........................ 600/372; 600/393; 600/411; 439/909; 128/908
[58] Field of Search ................................ 600/372, 373, 600/377, 384, 386, 393–395, 411, 382; 439/909; 128/901, 908; 607/119, 122, 152

[56] References Cited

U.S. PATENT DOCUMENTS

| | | | |
|---|---|---|---|
| 3,572,344 | 3/1971 | Bolduc | 600/732 |
| 4,280,507 | 7/1981 | Rosenberg . | |
| 4,951,672 | 8/1990 | Buchwald et al. . | |
| 4,991,580 | 2/1991 | Moore . | |
| 5,178,145 | 1/1993 | Rea | 600/372 |
| 5,209,233 | 5/1993 | Holland et al. | 128/653.2 |
| 5,217,010 | 6/1993 | Tsitlik et al. | 607/9 |
| 5,445,162 | 8/1995 | Ives . | |
| 5,782,241 | 7/1998 | Felblinger et al. | 600/509 |
| 5,916,162 | 6/1999 | Snelten et al. | 600/411 |

OTHER PUBLICATIONS

Van Genderingen et al., "Carbon–Fiber Electrodes and Leads for Electrocardiography During MR Imaging", p. 872, Radiology, Jun. 1989.

*Primary Examiner*—Linda C. M. Dvorak
*Assistant Examiner*—David M Ruddy
*Attorney, Agent, or Firm*—Jacox, Meckstroth & Jenkins

[57] ABSTRACT

A leadwire harness system is used for recording an electrocardiogram (ECG) during magnetic resonance imaging (MRI). The system includes a set of leadwires each having a nichrome wire helically wound on a bundle of glass or other high strength fibers and surrounded by an insulating jacket to provide for uniformly distributing the high resistance within each leadwire so that the eddy currents generated by the rapidly changing magnetic field are greatly reduced. The set of leadwires are twisted within a surrounding tube of foam insulation. The reduction of the eddy currents dramatically reduces MRI image distortion as well as the potential for localized heating and skin burns under the ECG electrodes used with the harness system.

22 Claims, 1 Drawing Sheet

DISTRIBUTED RESISTANCE LEADWIRE HARNESS ASSEMBLY FOR PHYSIOLOGICAL MONITORING DURING MAGNETIC RESONANCE IMAGING

RELATED APPLICATION

This application claims the benefit of provisional patent appication Ser. No. 60/069,147, filed Dec. 9, 1997.

BACKGROUND OF THE INVENTION

Magnetic Resonance Imaging (MRI) is a relatively new technique used in medicine to investigate in great detail the condition of the human body. The patient is typically placed supine on a moveable horizontal table which is moved through rapidly changing and intense magnetic fields. Detailed information on the interior of the body can be obtained by computer analysis of the magnetic resonance produced by the rapidly changing magnetic fields. In many instances, the information obtained from MRI is more detailed than the information available from the use of X-Ray and at less risk to the patient. Because the patient undergoing MRI is sick for one reason or another and because the MRI experience is often traumatic, it is important that the physiological state of the patient be monitored.

The room in which the MRI is performed is highly shielded, with monitoring equipment placed in an adjacent room. The patient connections are typically fed through the shielded wall to the monitoring equipment. While the shielding isolates the monitoring equipment from the intense, rapidly changing magnetic fields generated by the MRI equipment, the leadwires which extend from the patient and through the shielded wall are subjected to this intense magnetic field. The rapidly changing magnetic fields induce high level noise signals into the physiological monitoring leads, and these noise signals can interfere with MRI image, as well as the physiological monitoring image, and this can cause localized heating and skin burns under the physiological monitoring electrodes.

U.S. Pat. No. 4,991,580 discloses a method to improve the quality of an Electrocardiogram (ECG) by reducing the high level noise signals induced into the cardiac monitoring leads. This is accomplished by employing special circuitry in the room with the ECG monitoring equipment in order to reduce the noise and amplify the ECG signal. However, this patent does not address the problem of skin heating or burns that also result from the eddy currents that produce this noise.

U.S. Pat. No. 5,445,162 discloses a method to reduce the amount of magnetic metal and associated Electroencephalogram (EEG) equipment outside of the bore of the MRI magnet and possibly outside of the MRI room. The intent is to reduce distortion of the MRI and also to obtain an EEG during Magnetic Resonance Imaging. The patent mentions the induction of significant current flow in electrodes and wires within the magnetic field and the possibility of these currents producing localized heating or burns under EEG electrodes connected to the patient's scalp. However, this patent does not attempt to resolve the possibility of burns under the monitoring electrodes. A similar phenomena occurs under ECG electrodes connected to the patient and located within the rapidly changing magnetic fields of the MRI system.

Van Genderingen et al (Radiology 1989) discloses a system of using carbon fiber electrodes and leads for obtaining an ECG during cardiac gating with MRI. The primary goal was to reduce the amount of distortion of the gradient magnetic field and the corresponding image distortion and artifact caused when metallic electrodes and leads are used. The electrical resistance of the carbon fiber leads was around 1,000 ohms. While this resistance reduces distortion, it is insufficient to prevent patient burns.

U.S. Pat. No. 4,951,672 discloses a leadwire designed specifically to monitor ECG signals during MRI and provide protection from unwanted heating under monitoring electrodes. The patent recognizes the need for the ECG leadwires to have a high resistance in order to reduce the possibility of heating under the electrodes, but the solution was to mold metal film resistors, of the 33k ohm to 10k ohm range, in the electrode connector of the wire. Since this produced a hot spot at the electrode connector, the patent discloses the inclusion of resistor modules along the length of the wire. However, the resistor modules result in producing many hot spots. The patent also mentions that the resistance could be distributed over the length of the leadwire. From the drawings, this must mean that if enough resistor modules are added along the length of the wire, the heat can be evenly spread, thereby reducing the possibility of burns. In actual practice, this proposed solution cannot work well. As the multiple of resistor modules increases, so does the number of hot spots, and the resistance is not uniformly distributed along the length of the wire.

Pat. No. 4,280,507 discloses a "Patient Cable with Distributed Resistance Protection in Conductors". In this patent, the concept of distributed resistance is employed. However, the protection this device provides is protection of the ECG monitor circuitry from the extreme electrical pulses that are present at the patient's ECG electrode sites when the patient is defibrillated while still connected to the ECG monitor via the ECG electrodes and cable/wires. The device is not designed to provide patient protection from heating or burns. Moreover, the use of carbon loaded polymers for a distributed resistance conductor, limits how high of resistance can be employed and how tight of a resistance tolerance that can be maintained.

SUMMARY OF THE INVENTION

The present invention is directed to a leadwire harness system for obtaining physiological patient information during an MRI process, and which dramatically reducing the possibility of patient burns under the physiological monitoring electrodes, while also reducing image distortion on the MRI unit.

The above identified problem is solved by the current invention by making the leadwire conductor itself the high resistance. By using a high resistance nichrome conductor which is helically wound around a fiber core, the exact resistance per foot of finished wire can be very tightly controlled by the number of turns of the conductor per linear foot of finished wire stock. As a result, the resistance is distributed evenly and uniformly from one end of the wire to the other, which results in even heating of the wire from one end to the other, with no spots of high concentrated heat. The wire is jacketed by a high temperature plastic layer, and a multiple of the wires form one assembly which is jacketed by a tube of high temperature foam so that the patient is not in contact with any hot wire.

The present invention overcomes problems not completely resolved in the prior art. By providing a uniformly distributed higher-than-normal resistance within the ECG leadwire system, the effect of eddy currents generated by the rapidly changing magnetic field of the MRI unit, is greatly reduced. The reduction of these eddy currents dramatically reduces the potential for MRI image distortion and the localized heating and skin burns under ECG electrodes used in conjunction with this system, especially if the electrodes are non-magnetic and essentially non-metallic.

The present invention makes use of a considerably higher resistance, for example, on the order of 2,500 to 10,000 ohms per foot. Thus, for a six foot cable, this resistance totals around 15,000 to 60,000 ohms. As the resistance in the individual leads (e.g. RA, RL, LA, LL) increases, it becomes increasingly important for these resistances to be closely matched. The difference in the individual lead resistances will cause problems with the common mode noise rejection of the ECG monitor, if it becomes excessive. This means that the tolerance or variation of the individual leadwire resistances must be well controlled. In one embodiment, the distributed resistance between any two of the leadwires varies less than 1%.

DESCRIPTION OF THE PREFERRED EMBODIMENT

Figure 1:
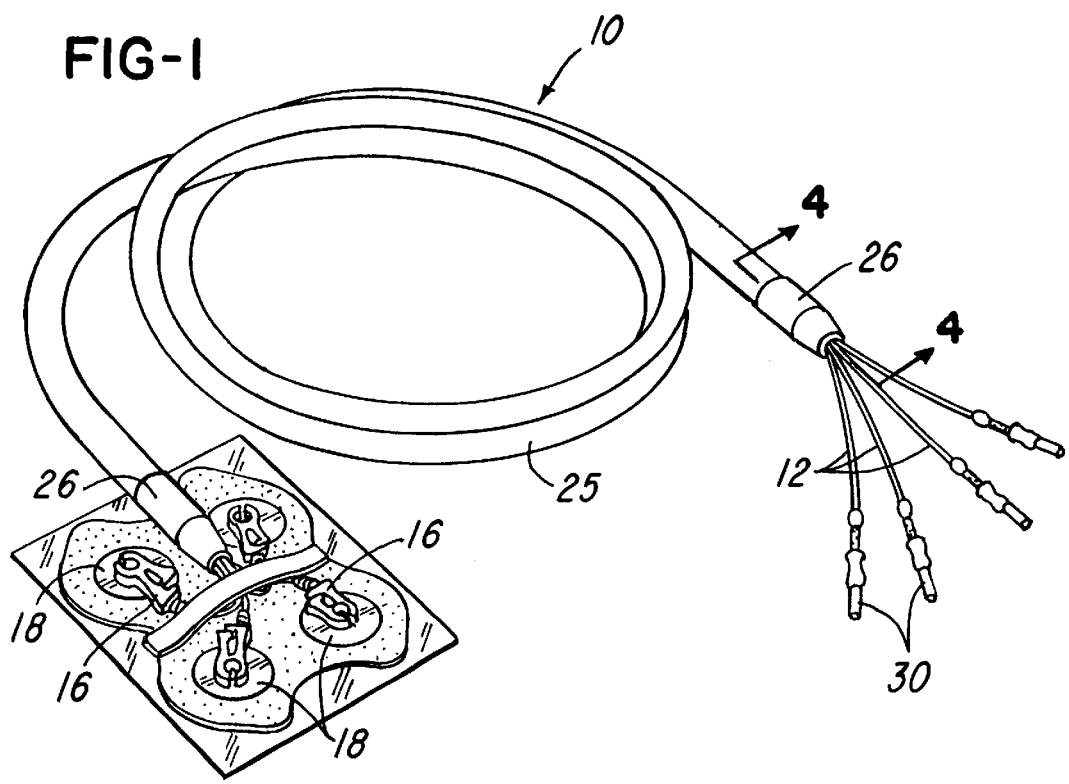
FIG. 1 is a perspective view of a leadwire harness system or assembly onstructed in accordance with the invention, and attached to a pad of medical electrodes.

In the preferred embodiment of the invention, a harness assembly 10 includes a set of four leadwires 12 each having a very fine nichrome conductor wire 13 with a diameter on the order of 0.0015 inch. Each wire 13 is helically wrapped or wound around a corresponding non-conductive fibrous core such as a glass fiber core 14 for support. Each core has a length of about six feet and provides both strength and flexibility which dramatically increases the tensile strength and flex life of the composite wire and core sub-assembly 15. The fiberglass core 14 also allows close control of the nichrome wrapped wire 13 which has a length of about 1440 inches for the six foot core. This produces a very uniformly distributed resistance along the length of the core 14. In one embodiment, the distributed resistance of each of the leadwires varies less than 5% along the length of the leadwire.

In one embodiment, each wire 13 has a resistance of 2,500 ohms per foot. However, the field strength of MRI units may eventually increase in order to shorten the MRI scan time. It is thus within the scope of the present invention to increase the resistance per foot in order to remain below the eddy current threshold for patient burns. This is readily accomplished by increasing the resistance per foot, for example, to 10,000 ohms per foot, if necessary. However, since higher resistance requires tighter tolerances in resistance, the illustrated embodiment is 2,500 ohms per foot.

Figure 2:
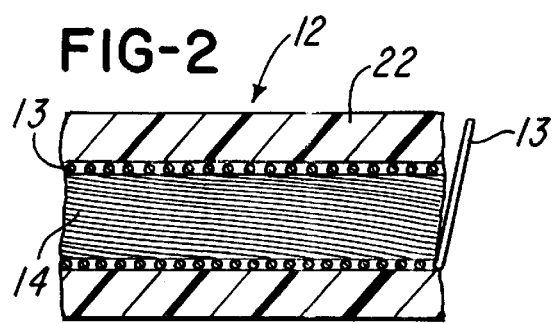
FIG. 2 is a greatly enlarged fragmentary section of one of the conductors shown in FIG. 1.
Figure 3:
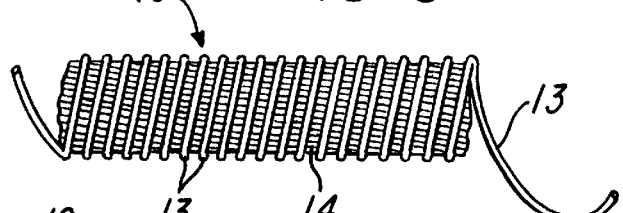
FIG. 3 is a fragmentary perspective view of the non-conductive fibrous core and helically wound resistance wire shown in FIG. 2.
Figure 4:
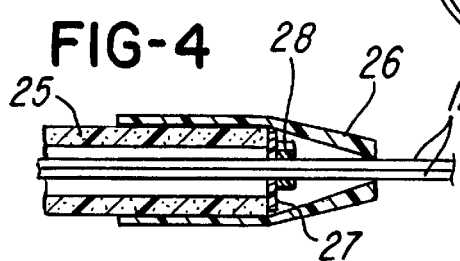
FIG. 4 is an enlarged fragmentary section of the harness assembly, taken generally on the line 4—4 of FIG. 1.

To provide a high level of patient safety, pinch-type electrode connectors 16 are connected to the patient ends of the wires 13 and form part of the harness assembly 10. The connectors 16 are both non-magnetic and non-metallic. The harness assembly 10 is preferably used with medical electrodes 18 which are also non-magnetic and essentially non-metallic with one leadwire 12 for each electrode 18. Since the individual wires 13 can become hot to the touch during use (as high as 150 degrees Celsius for short durations), each wire 13 is insulated with a high temperature plastic layer 22 (FIG. 2), such as ETFE or other comparable engineering grade polymer. In addition, the group of four leadwires 12 for the harness system 10 is jacketed by a soft, highly flexible, high temperature silicone foam tubing 25 (FIG. 4).

The electrode connector ends of the leadwires 12 are very short and extend from the foam insulation. As a result, the patient cannot come into contact with any component that has an elevated temperature. A tubular rubber-like collar 26 (FIG. 4) surrounds each end portion of the tubing 25 and encloses a washer 27 and a plastic band or tie 28 which is clamped to the leadwires 12. Metal terminal pins or connectors 30 are attached to the inner ends of the leadwires 12, as shown in FIG. 1.

The group of leadwires 12 of the assembly 10, with the individual conductor wires 13 being helically wound around their respective cores 14, are twisted or helically wound around each other from end to end to provide, preferably, about nine complete turns within the foam insulation tube 25 which has a length of about six feet. This twisted arrangement of the leadwires 12 causes the eddy currents to somewhat cancel each other and further helps to reduce the distortion of the gradient magnetic field and the corresponding distortion of the MRI image.

While the form of leadwire harness assembly and the method of producing the assembly constitute a preferred embodiment of the invention, it is to be understood that the invention is not limited to this precise form of harness assembly and method, and that changes may be made therein without departing from the scope and spirit of the invention as defined in the appended claims.

The invention having thus been described, the following is claimed:

1. An improved leadwire system adapted for connecting a plurality of physiological monitoring electrodes on a living body to a physiological monitoring device and for minimizing the risk of burns under the monitoring electrodes and for reducing image distortion on a scanning device, said leadwire system comprising a plurality of leadwires each including a high resistance conductor helically wound around an electrically insulating fibrous core, a layer of high temperature thermal insulating material surrounding each said conductor and providing a generally uniformly distributed high resistance along the length of each leadwire, said plurality of leadwires having means for reducing gradiant noise on the monitoring device, a jacket of high temperature thermal insulating material surrounding said plurality of leadwires, each said leadwire having one end portion adapted to be connected to a corresponding monitoring electrode, and each said leadwire having an opposite end portion adapted to be connected to an input of the monitoring device.

2. A leadwire system as defined in claim 1 wherein each of said leadwires has a substantially uniformly distributed electrical resistance of at least 2500 ohms per foot.

3. A leadwire system as defined in claim 1 wherein said electrical conductor of each said leadwire is substantially non-magnetic.

4. A leadwire system as defined in claim 3 wherein said conductor of each said leadwire comprises a nickel-chrome alloy.

5. A leadwire system as defined in claim 1 wherein said insulating fibrous core of each said leadwire comprises a bundle of glass fibers.

6. A leadwire system as defined in claim 1 wherein said plurality of leadwires are twisted around each other as a group between opposite ends of said jacket to provide said means for reducing gradiant noise.

7. A leadwire system as defined in claim 1 wherein the distributed resistance of each of said leadwires varies less than 5% along the length of said leadwire.

8. A leadwire system as defined in claim 1 wherein the distributed resistance between any two of said leadwires varies less than 1%.

9. A leadwire system as defined in claim 1 wherein said one end portion of each said leadwire is connected a by non-magnetic and non-metallic connector.

10. A leadwire system as defined in claim 1 wherein said jacket of high temperature thermal insulating material comprises an extruded tube of flexible foam material.

11. A leadwire system as defined in claim 1 wherein each of said leadwires has a substantially uniformly distributed electrical resistance within a range of about 2500 to 10,000 ohms per foot.

12. A leadwire system as defined in claim 1 and including a non-magnetic and non-metallic spring biased pinch connector attached to said one end portion of each said leadwire.

13. An improved leadwire system adapted for connecting a plurality of physiological monitoring electrodes on a living body to a physiological monitoring device and for minimizing the risk of burns under the monitoring electrodes and for reducing image distortion on a scanning device, said leadwire system comprising a plurality of leadwires each including a high resistance conductor helically wound around an electrically insulating fibrous core, a layer of high temperature thermal insulating material s surrounding each said conductor and providing a generally uniformly distributed high resistance along the length of each leadwire, said plurality of leadwires being twisted as a group for reducing gradiant noise on the monitoring device, a tubular jacket of high temperature thermal insulating material surrounding said twisted group of leadwires, a first releasable connector secured to one end portion of each said leadwire for releasably connecting said leadwire to a corresponding monitoring electrode, and a second connector secured to an opposite end portion of each said leadwire for releasably connecting said leadwire to an input of the monitoring device.

14. A leadwire system as defined in claim 13 wherein each of said leadwires has a substantially uniformly distributed electrical resistance of at least 2500 ohms per foot.

15. A leadwire system as defined in claim 13 wherein said electrical conductor of each said leadwire is substantially non-magnetic.

16. A leadwire system as defined in claim 15 wherein said conductor of each said leadwire comprises a nickel-chrome alloy.

17. A leadwire system as defined in claim 13 wherein the distributed resistance of each of said leadwires varies less than 5% along the length of said leadwire.

18. A leadwire system as defined in claim 13 wherein the distributed resistance between any two of said leadwires varies less than 1%.

19. A leadwire system as defined in claim 13 wherein said jacket of high temperature thermal insulating material comprises an extruded tube of flexible foam material.

20. A leadwire system as defined in claim 13 wherein each of said leadwires has a substantially uniformly distributed electrical resistance within a range of about 2500 to 10,000 ohms per foot.

21. A leadwire system as defined in claim 13 wherein said first connector comprises a non-magnetic and non-metallic spring biased pinch connector.

22. A leadwire system as defined in claim 13 wherein said group of leadwires has about nine complete turns within about six feet of said tubular jacket.

* * * * *